(12) United States Patent
Han et al.

(10) Patent No.: US 9,101,640 B2
(45) Date of Patent: Aug. 11, 2015

(54) USE OF DANSHENSU, NOTOGINSENOSIDE R1 OR THEIR COMBINATION IN PREPARATION OF MEDICAMENTS FOR PREVENTING AND TREATING DISEASES CAUSED BY MICROCIRCULATION DISORDER

(75) Inventors: Jingyan Han, Tianjin (CN); Jun Guo, Tianjin (CN); Jiying Yang, Tianjin (CN); Kai Sun, Tianjin (CN); Mingxia Wang, Tianjin (CN); Yu Zhang, Tianjin (CN); Yuying Liu, Tianjin (CN)

(73) Assignee: Tasly Pharmaceutical Group Co., Ltd., Tianjin (CN)

( * ) Notice: Subject to any disclaimer, the term of this patent is extended or adjusted under 35 U.S.C. 154(b) by 545 days.

(21) Appl. No.: 13/505,051

(22) PCT Filed: Nov. 4, 2010

(86) PCT No.: PCT/CN2010/078411
§ 371 (c)(1),
(2), (4) Date: Jun. 11, 2012

(87) PCT Pub. No.: WO2011/054301
PCT Pub. Date: May 12, 2011

(65) Prior Publication Data
US 2012/0295858 A1 Nov. 22, 2012

(30) Foreign Application Priority Data
Nov. 5, 2009 (CN) .......................... 2009 1 0071163

(51) Int. Cl.
*C07C 59/52* (2006.01)
*C07H 15/256* (2006.01)
*A61K 31/704* (2006.01)
*A61K 31/192* (2006.01)

(52) U.S. Cl.
CPC ............. *A61K 31/704* (2013.01); *A61K 31/192* (2013.01); *C07C 59/52* (2013.01); *C07H 15/256* (2013.01)

(58) Field of Classification Search
None
See application file for complete search history.

(56) References Cited

U.S. PATENT DOCUMENTS

2005/0037094 A1 2/2005 Yan et al.

FOREIGN PATENT DOCUMENTS

| CN | 1470255 A | 1/2004 |
| CN | 1729966 A | 2/2006 |
| CN | 101474185 A | 7/2009 |
| CN | 101485648 A | 7/2009 |
| CN | 101574357 A | 11/2009 |

OTHER PUBLICATIONS

Merriam-Webster's Collegiate Dictionary, published 1998 by Merriam-Webster, Incorporated, p. 924.*
Ling et al., "Preparation of Herbal Medicine Salvia miltiorrhiza Reduces Expression of Intercellular Adhesion Molecule-1 and Development of Atherosclerosis in Apolipoprotein E-Deficient Mice" Journal of Cardiovascular Pharmacology vol. 51 No. 1 pp. 38-44.*
Horie et al., "Herbal cardiotonic pills prevent gut ischemia/reperfusion-induced hepatic microvascular dysfunction in rats fed ethanol chronically" World Journal of Gastroenterology (2005).*
Chen, Wei-Xing et al., "The Effects of Notoginsenoside R1 on the Disfunction of Heptic Microvessels Introduced by Gut Ischemia Reperfusion", Tasly Microcirculation Research Center, Jan. 7, 2008.
Guo, et al., "Protective Effects of Dihydroxylphenyl Lactic Acid and Salvianolic Acid B on LPS-Induced Mesenteric Microcirculatory Disturbance in Rats," SHOCK, vol. 2, pp. 205-211, 2008.
Sun, et al., "Protective Effects of Ginsenoside Rb1, Ginsenoside Rg1, and Notoginsenoside R1 on Lipopolysaccharide-Induced Microcirculatory Disturbance in Rat Mesentery," ScienceDirect, Life Sciences 81, pp. 509-518 (2007).
Chen, Wei-Xing et al., "Effect of Notoginsenoside R1 on Hepatic Microcirculation Disturbance Induced by Gut Ischemia and Reperfusion," World J. Gastroenterol, World Journal of Gastroenterology, Jan. 7, 2008, 14(1): 29-37, ISSN 1007-9327.
Japanese Office Action dated Sep. 16, 2014 of correspondence Japanace Application No. 2012-537291.

* cited by examiner

*Primary Examiner* — Eric Olson
(74) *Attorney, Agent, or Firm* — Lando & Anastasi, LLP

(57) ABSTRACT

The present invention relates to a new use of traditional Chinese drug products of Danshensu (DLA), Notoginsenoside R1 (R1) and their combination, in particular to the therapeutic and preventive effects of DLA, R1 and their combination on the diseases caused by microcirculation disorder.

13 Claims, 4 Drawing Sheets

* represents significant difference compared to Sham operation group
# represents significant difference compared to I/R group

USE OF DANSHENSU, NOTOGINSENOSIDE R1 OR THEIR COMBINATION IN PREPARATION OF MEDICAMENTS FOR PREVENTING AND TREATING DISEASES CAUSED BY MICROCIRCULATION DISORDER

FIELD OF THE INVENTION

The present invention relates to a new use of traditional Chinese drug products of Danshensu, Notoginsenoside R1 and their combinations, in particular to the therapeutic and preventive effects of Danshensu, Notoginsenoside R1 and their combinations on the diseases caused by microcirculation disorder.

BACKGROUND OF THE INVENTION

Ischemia-reperfusion (I/R) injury is believed to be the main pathological basis for injuries occurred after interventional therapy, surgical operation and thrombolysis. As found in numerous studies, the adhesion of the leukocytes to the vascular endothelial cells and the mast cells degranulation after I/R constitute the main pathological factors for vascular injury.

Microcirculation is a vascular bed, which accounts for 90% of in vivo vessels, including arterioles, capillaries and venules etc. It is thought to be an important part to maintain metabolism. Various types of factors, such as allergic diseases, hyperlipidemia, hypertension, infection, mental stimulation, traumatic injury, operation and interventional therapy, can induce microcirculation disorder. The microcirculation disorder is a complicated process comprising a series of symptoms as follows: variation of vascular diameters; production of peroxides; expression of vascular endothelial adhesion factor ICAM-1 and leukocyte adhesion factor CD11b/CD18; adhesion of leukocytes to vascular endothelial cells; leakage of plasma albumin; release of vasoactive substances, e.g. TNF-α, histamine, 5-HT, inflammatory factors through degranulation of extravascular mast cells; formation of thrombus and bleeding etc.

Mast cells degranulation is a main pathological factor in type I allergy, said Mast cells degranulation is considered to be a main pathological basis for pollinosis, skin diseases, asthma and diarrhea.

Danshensu (3,4-dihydroxyphenyl lactic acid. DLA) and Notoginsenoside R1 (R1) are one of the major active components of *Radix Salviae Militiorrhizae* (Danshen) and *Panax Notoginseng* (Sanqi) in Compound Salvia drop pills (Cardiotonic Pills®, CP), respectively. Our previous studies had demonstrated that CP had ameliorative effects on rat's heart, liver and mesenteric microcirculation disorder caused by I/R. Hence, it had been proven that total salvianolic acids (the major active components in Danshen) and *Panax notoginseng* saponins (the major active components in Sanqi) had ameliorative effects on rat's mesenteric microcirculation disorder caused by I/R. However, it is still unknown at present on which factors of microcirculation disorder DLA and R1 (the major active components of Danshen and Sanqi in CP, respectively) will act, and whether the combinations of the above two components in different ratios have synergistic action. Due to this, a dynamic and visual method is used in the present study to analyze in which factors DLA, R1 and their combinations can ameliorate rat's mesenteric microcirculation disorder caused by I/R.

After the experiments, the inventors found that DLA, R1 and their combinations can ameliorate the mesenteric microcirculation disorder caused by I/R so that the therapeutic and/or preventive effects on microcirculation disorder-caused diseases can be exhibited, and thus a traditional Chinese medicament formulation is also provided.

DESCRIPTION OF THE INVENTION

The inventors have found a new use of DLA. R1 and their combinations. In particular, the invention relates to therapeutic and preventive effects of DLA, R1 and their combinations on the mesenteric microcirculation disorder caused by I/R, thus DLA, R1 and their combinations can be used in treating and/or preventing microcirculation disorder-caused diseases, for example, allergic diseases, hyperlipidemia, hypertension, infection, mental stimulation, traumatic injury, pollinosis, skin diseases, asthma, diarrhea, microcirculation disorder caused by operation or interventional therapy etc.

The inventors have found that a pre-administration and post-administration with DLA. R1 and their combinations may inhibit the rolling and adhesion of leukocytes in venules and can also inhibit the mast cells degranulation after I/R.

In particular, the inventors have found that a pre-administration with DLA can inhibit the following symptoms caused by I/R: an increase in the number of leukocytes rolling along venular walls, an increase in the number of leukocytes adhered to inner walls of venules, an increase in the number of leukocytes emigrated from venules, a production of peroxides in venular walls, a leakage of plasma albumin from venules and an increase in a percentage of mast cells degranulation. A post-administration with DLA can inhibit the following symptoms caused by I/R: an increase in the number of leukocytes adhered to inner walls of venules, an increase in the number of leukocytes emigrated from venules, a production of peroxides in venular walls and a leakage of plasma albumin from venules.

In particular, the inventors have found that a pre-administration or post-administration with R1 can inhibit the following symptoms caused by I/R: an increase in the number of leukocytes adhered to inner walls of venules, an increase in the number of leukocytes emigrated from venules, and an increase in a percentage of mast cells degranulation.

The inventors have found that a pre-administration or post-administration with the combinations of DLA and R1 can inhibit the following symptoms caused by I/R: an increase in the number of leukocytes adhered to inner walls of venules, an increase in the number of leukocytes emigrated from venules, a production of peroxides in venular walls, a leakage of plasma albumin from venules and an increase in a percentage of mast cells degranulation.

The inventors have found that a post-administration with the combination of DLA and R1 in a weight ratio of 4:1 has particularly significant inhibition effects on the leakage of plasma albumin from venules caused by I/R.

The inventors have found that a pre-administration with the combination of DLA and R1 in a weight ratio of 4:1 has particularly significant inhibition effects on the production of peroxides in venular walls caused by I/R.

According to the present invention, said DLA is one component of Danshen, a traditional Chinese drug. DLA is either commercially available, or can be prepared in light of the methods known in the prior art. Said R1 is one component of another traditional Chinese drug of Sanqi. R1 is either commercially available, or can be prepared in light of the methods known in the prior art. Both of the two components are well-known in the prior art. DLA and R1 used in the present invention are products complying with the pharmaceutical standards with a preferable purity of more than 50 wt %, more preferable more than 90 wt %, most preferable more than 98 wt %.

According to the present invention, said medicine is a pharmaceutical composition prepared by using the aforesaid DLA, R1 or their combinations as active component(s).

If needed, the pharmaceutical composition of the present invention can contain pharmaceutically acceptable carrier(s). Wherein, said DLA, R1 or their combinations can be used as active component(s) of the medicine, with a weight ratio of 0.1-99.9 wt % in the total preparation and the balanced is pharmaceutically acceptable carrier(s). The pharmaceutical composition of the present invention is presented as a unit dosage form. Said unit dosage form refers to a unit of preparation, e.g. one tablet, one capsule, one bottle of oral solution, one bag of granule and one injection.

Said combinations refer to the combinations of DLA and R1 in weight ratios of (1~4):(4~1), preferably (1~2):(2~1), most preferably 1:1.

According to the present invention, said pharmaceutical composition can be prepared into any one of the pharmaceutically acceptable dosage forms. The dosage forms include: tablets, e.g. sugar-coated tablets, film-coated tablets and enteric-coated tablets; capsules, e.g. hard capsules and soft capsules; oral solutions; buccal tablets; granules; granules taken after dissolving in boiling water; pills; powders, pastes, e.g. ointments, plasters; pellets; suspensions; pulvis; liquors, e.g. injections; suppositories; creams; sprays; drops and patches.

According to the present invention, the orally-administrated preparations can contain conventional excipient(s), e.g. binding agents, bulking agents, diluents, tablet-pressing agents, lubricants, disintegrating agents, colorants, flavoring agents, wetting agents, and if necessary, coating agents so that the tablets can be coated.

Suitable bulking agents include cellulose, mannitol, lactose and other analogous bulking agents. Suitable disintegrating agents include starch, polyvinylpyrrolidone (PVP) and starch derivatives (such as sodium starch glycollate). Suitable lubricants include, such as magnesium stearate. Suitable pharmaceutically acceptable wetting agents include sodium dodecyl sulfate.

Usually, oral solid preparations can be prepared by conventional methods, such as blending, filling and tablet-pressing, etc. Being blended repeatedly allows the active substance distribute uniformly into those compositions having a large amount of bulking agent.

According to the present invention, oral liquid preparations can be, for example water-soluble or oil-soluble suspensions, solutions, emulsions, syrups or elixirs, or dried products that can be reconstituted with water or other suitable carriers before using. The liquid preparations can contain conventional additives, for example, suspending agents, e.g. sorbitol, syrup, methylcellulose, gelatin, hydroxyethyl cellulose, carboxymethyl cellulose, aluminum stearate gel or hydrogenated edible fat; emulsifying-agents, e.g. lecithin, sorbitan monoleate or arabic gum; non-aqueous carriers which can be edible oil, e.g. almond oil, fractionated coconut oil, esters of glycerol, propylene glycol or ethanol; and preservatives, e.g. methyl paraben, nipasol or sorbic acid. And if necessary, conventional scenting agents or colorants can be included.

As for the injections, the prepared liquid unit dosage form contains the active component(s) of the present invention and sterile carrier(s). According to the type of the carrier(s) and concentration of the active component(s), said active component(s) can be dissolved or suspended. Generally, the solutions are prepared by dissolving the active component(s) in the carriers, sterilizing by filtering, loading into a suitable vial or ampoule, and sealing. Some pharmaceutically acceptable vehicles, e.g. local anesthetics, preservatives and buffering agents can also be added into the carriers. In order to improve the stability, the composition of the present invention can be frozen after being loaded into the vial and then treated in vacuum to remove water.

According to the present invention, when said composition is prepared into a formulation into which the pharmaceutically acceptable carriers can be added. Said carriers are selected from sugar alcohol, e.g. mannitol, sorbitol, xylitol; amino acid, e.g. cysteine hydrochloride, methionine, glycine; Vitamin C; EDTA disodium salt. EDTA calcium sodium salt; inorganic salts, e.g. carbonates, acetates, phosphates of the monovalent alkali metals or aqueous solutions thereof, sodium chloride, potassium chloride, sodium pyrosulfite, sodium bisulfite, sodium thiosulfate, calcium carbonate, calcium bicarbonate; stearates, e.g. calcium stearate, magnesium stearate; inorganic acids, e.g. hydrochloric acid, sulfuric acid, phosphoric acid; organic acids, e.g. acetic acid; organic acid salts, e.g. sodium lactate; oligosaccharides, polysaccharides, celluloses and derivatives thereof, e.g. maltose, glucose, fructose, dextran, sucrose, lactose, cyclodextrin (such as β-cyclodextrin), starch; silicon derivatives; alginate; gelatin; PVP, glycerol; Tween-80; agar; surfactants; polyethylene glycol; phospholipids materials; Kaolin; talc powder etc.

According to the present invention, the medical usage and the dosage of said composition are determined by patients' conditions.

Therapeutic and preventive use of the present invention is confirmed via the following experiments.

Materials and Methods

1. Reagents

DLA and R1 were provided by Fenashanjian Pharmaceutical Inc. (Kunming, China). Toluidine Blue (TB), dihydrorhodamine (DHR) and FITC-labeled albumin were purchased from Sigma Inc.

2. Animals

Wistar male rats weighing 200~250 g were provided by Saitama Laboratory Animal Center (Japan). The rats were placed under the conventional breeding environment (temperature: $24\pm1°$ C., relative humidity: $50\pm5\%$, alternative lighting per 12 hours). All of the animals were treated according to Animal Handling and Ethical Guidelines prescribed by Department of Medicine, Keio University (Japan). Before the experiments, the animals were fasted but supplied with water for 12 hours.

3. Establishment of the I/R Model and Administration

I/R Group:

The rats were anesthetized by intraperitoneal injection of pentobarbital sodium (30 mg/kg body weight (BW)). PE venous cannulas (#3) were cannulated into the right jugular of the rats and detained. The abdomen of each rat was incised in a length of 20-30 mm along the midline. The ileum near the ileocecal junctions was gently taken out and unfolded onto the object stage mounted with glass slides. The unfolded mesenteries were continuously dripped with Krebs-Ringer buffering solution at $37°$ C. The microcirculatory dynamics of the mesenteries was observed under white light (12V, 100 W) using an inverted biomicroscope (Diaphot TMD-2S, Nikon, Tokyo) placed in the thermostat at $37°$ C. Observation sites were selected under 20× object lens, and a video recording system with a time-displaying function was used to record what had been observed on S-VHS tape and preserved. The microcirculation vascular beds having non-branched regions of the venules with the diameters ranging between 25 μm and 35 μm were selected as the sites for observation, and said non-branched regions of the venules had a length of 200 μm or longer. Normal saline was administered at 20 min before ischemia until the end of the observation by continuously intravenous drip via jugular at a dosage of 5 mg/kg/h. PE cannulas were used to ligate non-circulatory mesenteric arteries and veins, so as to observe the arteries and veins for 10 min, and then the ligation was lifted. Time was adjusted to zero and the microcirculatory dynamics under the same visual field was continuously observed for 60 min.

Sham Operation Group (Sham Group):

Anesthesia and laparotomy to the rats in this group were performed in the same way to that of I/R rats. Mesenteries were taken out for observing without I/R treatment. Normal saline was administered at 20 min before ischemia until the end of the observation by continuously intravenous drip via jugular at a dosage of 5 mg/kg/h.

DLA Pre-Administration Group (DLA+I/R Group):

DLA was administered at 20 min before ischemia until the end of the observation by continuously intravenous drip via jugular at a dosage of 5 mg/kg/h.

R1 Pre-Administration Group (R1+I/R Group):

R1 was administered at 20 min before ischemia until the end of the observation by continuously intravenous drip via jugular at a dosage of 5 mg/kg/h.

DR (DLA+R1) (4:1) Pre-Administration Group (DR (4:1)+I/R Group):

The combination of DLA and R1 in a weight ratio of 4:1 was administered at 20 min before ischemia until the end of the observation by continuously intravenous drip via jugular at a dosage of 5 mg/kg/h.

DR (1:1) Pre-Administration Group (DR (1:1)+I/R Group):

The combination of DLA and R1 in a weight ratio of 1:1 was administered at 20 min before ischemia until the end of the observation by continuously intravenous drip via jugular at a dosage of 5 mg/kg/h.

DR (1:4) Pre-Administration Group (DR (1:4)+I/R Group):

The combination of DLA and R1 in a weight ratio of 1:4 was administered at 20 min before ischemia until the end of the observation by continuously intravenous drip via jugular at a dosage of 5 mg/kg/h.

DLA Post-Administration Group (DLA+I/R Group):

DLA was administered at 10 min after I/R until the end of the observation by continuously intravenous drip via jugular at a dosage of 5 mg/kg/h.

R1 Post-Administration Group (R1+I/R Group):

R1 was administered at 20 min after ischemia until the end of the observation by continuously intravenous drip via jugular at a dosage of 5 mg/kg/h.

DR (4:1) Post-Administration Group (DR (4:1)+I/R Group):

The combination of DLA and R1 in a weight ratio of 4:1 was administered at 20 min after ischemia until the end of the observation by continuously intravenous drip via jugular at a dosage of 5 mg/kg/h.

DR (1:1) Post-Administration Group (DR (4:1)+I/R Group):

The combination of DLA and R1 in a weight ratio of 1:1 was administered at 20 min after ischemia until the end of observation by continuously intravenous drip via jugular at a dosage of 5 mg/kg/h.

DR (1:4) Post-Administration Group (DR (1:4)+I/R Group):

The combination of DLA and R1 in a weight ratio of 1:4 was administered at 20 min after ischemia until the end of the observation by continuously intravenous drip via jugular at a dosage of 5 mg/kg/h.

Wherein, 6 rats in each group were taken out, these rats were used for observing the following aspects: the venular diameters; leukocytes rolling, adhesion, and emigration and DHR fluorescence intensities of the venular walls. Besides, another 6 rats in each group were used for observing plasma albumin leakage and mast cells degranulation.

4. Observation on Microcirculatory Dynamics

Microcirculatory dynamics was continuously recorded using an inverted biomicroscope COD recording system (CC-090, Flovel, Tokyo) and SIT fluorescent camera (C-2400-08, Hamamatsu Photonics, Hamamatsu).

Measurement of the Diameters of Vessels 3 sites of the mesenteric venules were measured using Image-Pro Plus 5.0 software from the replayed CD records at the following time points: before ischemia and 1 min, 10 min, 20 min, 30 min, 40 min, 50 min and 60 min after the beginning of the reperfusion. The average diameters were calculated.

Counting of Leukocytes Rolling Along Inner Walls of Venules

The leukocytes roiling along the inner walls of the venules in a length of 200 μm within 10 s was counted from the replayed images at the following time points: before ischemia, and 1 min, 10 min, 20 min, 30 min, 40 min, 50 min and 60 min after the beginning of the reperfusion.

Counting of Leukocytes Adhered to Venular Walls

The leukocytes adhered to the venules which stayed at one site on the venular walls for at least 30 s the adherent leukocytes) was counted from the replayed images at the following time points: before ischemia, and 1 min, 10 min, 20 min, 30 min, 40 min, 50 min and 60 min after the beginning of the reperfusion. The number of the leukocytes adhered to the venules having a length of 100 μm was calculated.

Counting of Leukocytes Emigrated from Venules

The number of the leukocytes emigrated from the mesenteric venules was observed and counted from the replayed images at the following time points: before ischemia, and 1 min, 10 min, 20 min, 30 min, 40 min, 50 min and 60 min after the beginning of the reperfusion.

Measurement of DHR Fluorescence Intensities of Venular Walls

The $H_2O_2$-sensitive fluorescent probes DHR (10 μm) were continuously dripped onto the surfaces of the rat's mesenteries to be observed. An inverted fluorescence microscope (DM-IRB, Leica, Germany) with an excitation wavelength at 455 nm and a mercury lamp as an excitation source (100 W) was used. The images were recorded with a CD camera at the following time points: before ischemia, and 1 min, 10 min, 20 min, 30 min, 40 min, 50 min and 60 min after the beginning of the reperfusion. The fluorescence intensities of the venular wall and the extravascular interstitial substance were measured with a Image-Pro Plus 5.0 software. The charming value between the fluorescence intensity of the venular wall and that of the extravascular interstitial substance before ischemia was taken as a baseline. The ratio of the changing value at each time point to the baseline were calculated, which was used to indicate the changing rate of the DHR fluorescence intensities of the rat's mesenteric venular walls.

Measurement of the Albumin Leakage from Venules

Another 6 rats in each group were taken out, and the FITC-labeled bovine serum albumin (50 mg/kg) was given by slowly intravenous bolus via the jugulars of the rats. After 10 min of the basic observation, an inverted fluorescence microscope (DM-IRB, Leica, Germany) with an excitation wavelength at 455 nm and a mercury lamp as an excitation source (100 W) was used. The FITC fluorescence images of the venules and the extravascular interstitial substances were continuously recorded with a CD camera at the following time points: before ischemia, and 1 min, 10 min, 20 min, 30 min, 40 min, 50 min and 60 min after the beginning of the reperfusion. The fluorescence intensities of the venular wall and the adjacent extravascular interstitial substance were measured with a Image-Pro Plus 5.0 software. The ratio of the FITC fluorescence intensity of the venular wall to that of the extravascular interstitial substance before ischemia was taken as a baseline. The ratio of the value at each time point to the baseline was calculated to indicate the change rate of the albumin leakage in the mesentery venules of the rats. The value at each time point can be expressed by the following equation: $R_t=P_t/P_0$, wherein $R_t$ represents the ratio of $P_t$ to $P_0$ at a certain time point, $P_t$ represents the ratio of the fluorescence intensity of the venular wall to that of the extravascular interstitial substance at this time point, and $P_0$ represents the ratio of the fluorescence intensity of the venular wail to that of the extravascular interstitial substance at 0 min.

Percentage of Mast Cells Degranulation 0.1% toluidine blue (TB) was dripped onto the observation sites 60 min after the beginning of the reperfusion and recorded with a CCD camera. The number of non-degranulated mast cells and degranulated mast cells in 5 visual fields were counted using 20× objective lens, the percentages of the degranulated mast cells to the total mast cells were calculated, which was regarded as the percentages of mast cells degranulation.

5. Statistical Analysis

All of the measured values were analyzed by one-way analysis of variance (ANOVA). The ongoing change of each group was analyzed with T-test, and the comparisons between any two groups among these groups were performed with F-test. All of the measured values were presented as mean±SE, and P<0.05 indicates a statistical significance.

DESCRIPTION OF DRAWINGS

In FIG. 1, Sham indicates Sham operation group; I/R, I/R group; DLA+I/R, DLA pre-administration group; R1+I/R, R1 pre-administration group; DR(4:1)+I/R, the combination of DLA and R1 in a weight ratio of 4:1 pre-administration group; DR(1:1)+I/R, the combination of DLA and R1 in a weight ratio of 1:1 pre-administration group; DR(1:4)+I/R, the combination of DLA and R1 in a weight ratio of 1:4 pre-administration group; I/R+DLA, DLA post-administration group; I/R+R1. R1 post-administration group; I/R+DR (4:1), the combination of DLA and R1 in a weight ratio of 4:1 post-administration group; I/R+DR (1:1), the combination of DLA and R1 in a weight ratio of 1:1 post-administration group; I/R+DR (1:4), the combination of DLA and R1 in a weight ratio of 1:4 post-administration group. The results are expressed as mean±SE. * represents P<0.05, compared to the Sham group; # represents P<0.05, compared to the I/R group.

In FIG. 2, Sham indicates Sham operation group; I/R, I/R group; DLA+I/R, DLA pre-administration group; R1+I/R, R1 pre-administration group; DR(4:1)+I/R, the combination of DLA and R1 in a weight ratio of 4:1 pre-administration group; DR(1:1)+I/R, the combination of DLA and R1 in a weight ratio of 1:1 pre-administration group; DR(1:4)+I/R, the combination of DLA and R1 in a weight ratio of 1:4 pre-administration group; I/R+DLA. DLA post-administration group; I/R+R1, R1 post-administration group; I/R+DR (4:1), the combination of DLA and R1 in a weight ratio of 4:1 post-administration group; I/R+DR (1:1), the combination of DLA and R1 in a weight ratio of 1:1 by post-administration group; I/R+DR (1:4), the combination of DLA and R1 in a weight ratio of 1:4 post-administration group. The results are expressed as mean±SE. * represents P<0.05, compared to the Sham group; # represents P<0.05, compared to the I/R group.

In FIG. 3, Sham indicates Sham operation group; I/R, I/R group; DLA+I/R, DLA pre-administration group; R1+I/R, R1 pre-administration group; DR(4:1)+I/R, the combination of DLA and R1 in a weight ratio of 4:1 pre-administration group; DR(1:1)+I/R, the combination of DLA and R1 in a weight ratio of 1:1 pre-administration group; DR(1:4)+I/R, the combination of DLA and R1 in a weight ratio of 1:4 pre-administration group; I/R+DLA. DLA post-administration group; I/R+R1. R1 post-administration group; I/R+DR (4:1), the combination of DLA and R1 in a weight ratio of 4:1 post-administration group; I/R+DR (1:1), the combination of DLA and R1 in a weight ratio of 1:1 post-administration group; I/R+DR (1:4), the combination of DLA and R1 in a weight ratio of 1:4 post-administration group. The results are expressed as mean±SE. * represents P<0.05, compared to the Sham group; # represents P<0.05, compared to the I/R group.

In FIG. 4, Sham indicates Sham operation group; I/R, I/R group; DLA+I/R, DLA pre-administration group; R1+I/R. R1 pre-administration group; DR(4:1)+I/R, the combination of DLA and R1 in a weight ratio of 4:1 pre-administration group; DR(1:1)+I/R, the combination of DLA and R1 in a weight ratio of 1:1 pre-administration group; DR(1:4)+I/R, the combination of DLA and R1 in a weight ratio of 1:4 pre-administration group; I/R+DLA, DLA post-administration group; I/R+R1. R1 post-administration group; I/R+DR (4:1), the combination of DLA and R1 in a weight ratio of 4:1 post-administration group; I/R+DR (1:1), the combination of DLA and R1 in a weight ratio of 1:1 post-administration group; I/R+DR (1:4), the combination of DLA and R1 in a weight ratio of 1:4 post-administration group. The results are expressed as mean±SE. * represents P<0.05, compared to the Sham group; # represents P<0.05, compared to the I/R group.

FIG. 5A illustrates the effects of a pre-administration with DLA, R1 or their combinations on the production dynamics of peroxides in the mesenteric venular walls of the rats after I/R. During the whole period of the observation, there are no obvious changes in DHR fluorescence intensities of the venular walls in Sham group. After the beginning of reperfusion, DHR fluorescence intensities of the venular walls began and continued to increase in I/R group. A pre-administration with R1 had no significant inhibitory effects on the production of peroxides in the mesenteric venular walls of the rats after I/R. In contrast, the pre-administration of DLA or each combination had significant inhibitory effects on the production of peroxides in the mesenteric venular walls after I/R. Wherein, a pre-administration of the combination of DLA and R1 in a weight ratio of 4:1 had the strongest inhibitory effect.

FIG. 5B illustrates the effects of a post-administration with DLA, R1 and their combinations on the production of peroxides in the mesenteric venular walls of the rats after I/R. A post-administration with R1 had no significant inhibitory effects on the production of peroxides in the mesenteric venular walls after I/R. In contrast, a post-administration with DLA or each combination had significant inhibitory effects on the production of peroxides in the mesenteric venular walls of the rats after I/R.

In FIG. 6, Sham indicates Sham operation group; I/R, I/R group; DLA+I/R, DLA pre-administration group; R1+I/R, R1 pre-administration group; DR(4:1)+I/R, the combination of DLA and R1 in a weight ratio of 4:1 pre-administration group; DR(1:1)+I/R, the combination of DLA and R1 in a weight ratio of 1:1 pre-administration group; DR(1:4)+I/R, the combination of DLA and R1 in a weight ratio of 1:4 pre-administration group; I/R+DLA, DLA post-administration group; I/R+R1, R1 post-administration group; I/R+DR (4:1), the combination of DLA and R1 in a weight ratio of 4:1 post-administration group; I/R+DR (1:1), the combination of DLA and R1 in a weight ratio of 1:1 post-administration group; I/R+DR (1:4), the combination of DLA and R1 in a weight ratio of 1:4 post-administration group. The results are expressed as mean±SE. * represents P<0.05, compared to the Sham group; # represents P<0.05, compared to the I/R group.

In FIG. 7, Sham indicates Sham operation group, I/R, I/R group; DLA-FUR. DLA pre-administration group; R1+I/R, R1 pre-administration group; DR (4:1)+I/R, the combination of DLA and R1 in a weight ratio of 4:1 pre-administration group; DR (1:1)+I/R, the combination of DLA and R1 in a weight ratio of 1:1 pre-administration group; DR (1:4)+I/R, the combination of DLA and R1 in a weight ratio of 1:4 pre-administration group; I/R+DLA, DLA post-administration group; I/R+R1, R1 post-administration group; I/R+DR (4:1), the combination of DLA and R1 in a weight ratio of 4:1 post-administration group; I/R-FOR (1:1), the combination of DLA and R1 in a weight ratio of 1:1 post-administration group; I/R+DR (1:4), the combination of DLA and R1 in a weight ratio of 1:4 post-administration group. The results are expressed as mean±SE. * represents P<0.05, compared to the Sham group; # represents P<0.05, compared to the I/R group.

CONCLUSIONS

Figure 1:
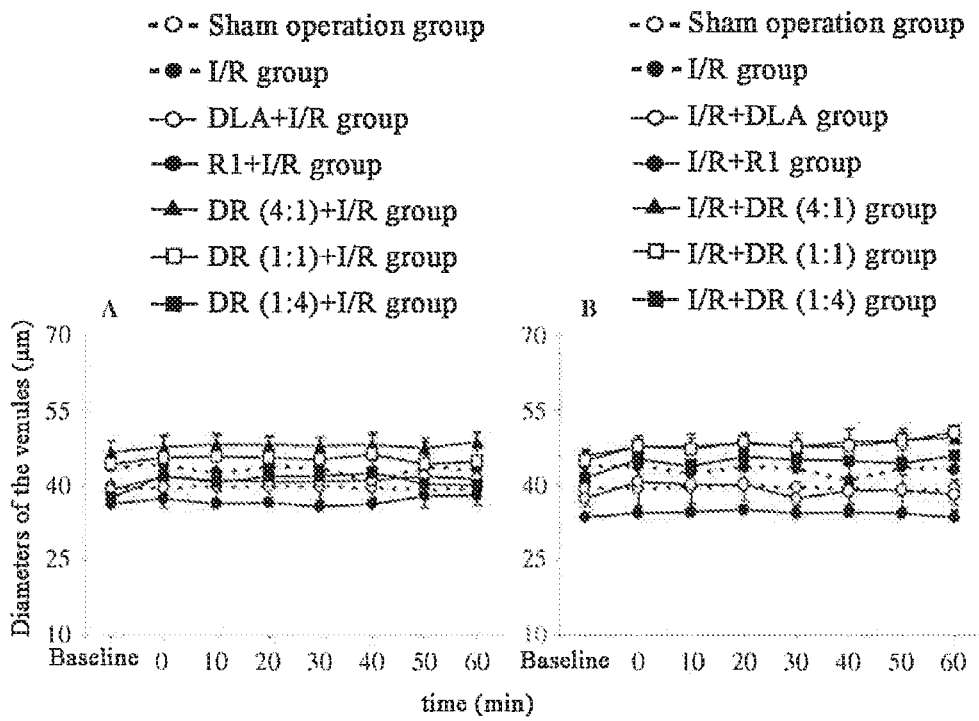
FIG. 1 illustrates the effects of DLA. R1 and their combinations on the diameters of the mesenteric venules in the rats after I/R. During the whole period of the observation, no significant changes on the diameters of the mesenteric venules in the rats in I/R group were detected. A pre-administration or post-administration with DLA, R1 and their combinations did not cause the significant changes on the diameters of the mesenteric venules in the rats after reperfusion.
Figure 2:
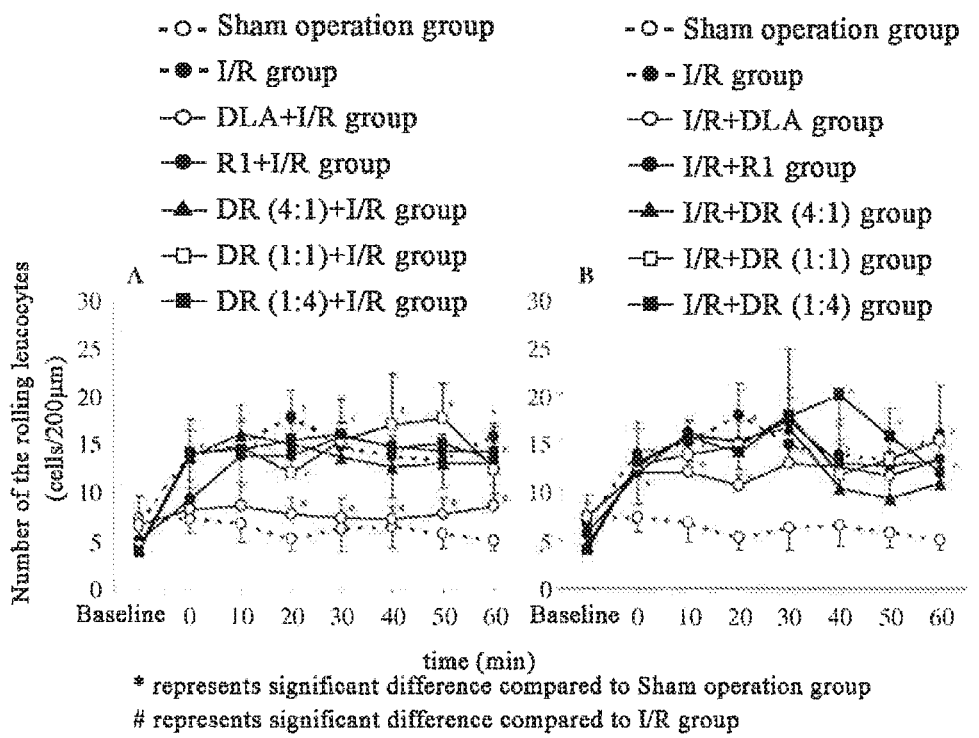
FIG. 2 illustrates the effects of DLA, R1 and their combinations on the leukocytes rolling in the mesenteric venules of the rats caused by I/R. The number of the leukocytes rolling along the mesenteric venular walls of the rats after I/R increased significantly. A pre-administration with DLA can apparently suppress the leukocytes rolling along the mesenteric venular walls caused by I/R. A pre-administration or post-administration with R1 or the combinations of DLA and R1 had no significant inhibitory effects on the leukocytes rolling along the mesenteric venular walls caused by I/R.
Figure 3:
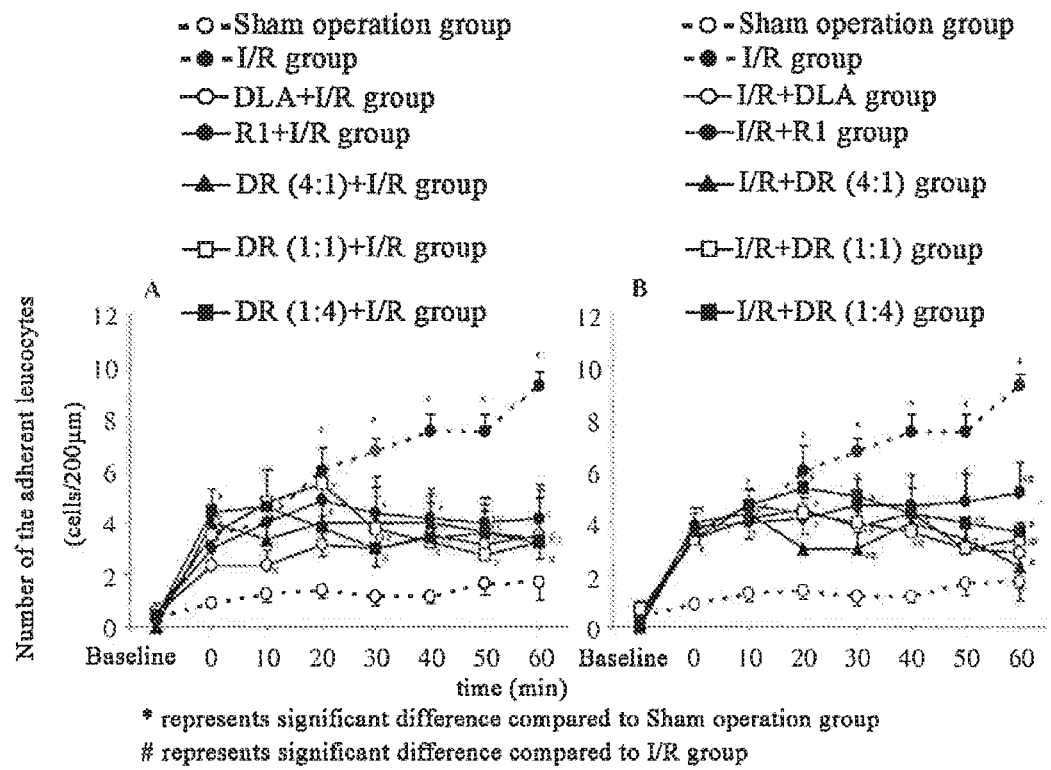
FIG. 3 illustrates the effects of DLA, R1 and their combinations on the leukocytes adhered to the mesenteric venules of the rats caused by I/R. Only a few of leukocytes adhered to the mesenteric venules were observed during the whole period of the observation in Sham group. There were numerous leukocytes adhered to the mesenteric venules of the rats in I/R group in the early stage of the reperfusion. With the ongoing process of the reperfusion, the adherent leukocytes increased gradually. A pre-administration or post-administration with DLA. R1 and their combinations had significant inhibitory effects on an increase in the number of the leukocytes adhered to the mesenteric venules of the rats caused by I/R.
Figure 4:
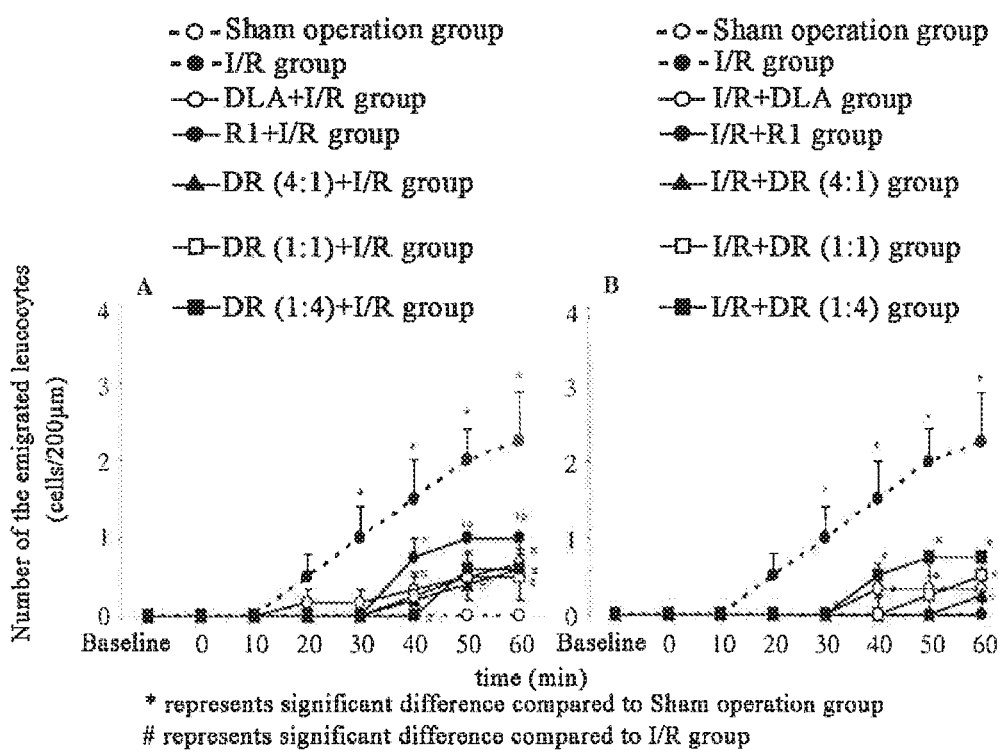
FIG. 4 illustrates the effects of DLA. R1 and their combinations on the emigration of leukocytes from the mesenteric venules of the rats caused by I/R. During the whole period of the observation, no emigrated leukocyte from the mesenteric venules was observed. Within 30 min after reperfusion in I/R group, the leukocytes emigrated from the mesenteric venules increased apparently and continued to increase until the end of this observation. A pre-administration or post-administration of DLA. R1 and their combinations had significant inhibitory effects on the emigration of the leukocytes from the mesenteric venules of the rats after I/R.
Figure 5:
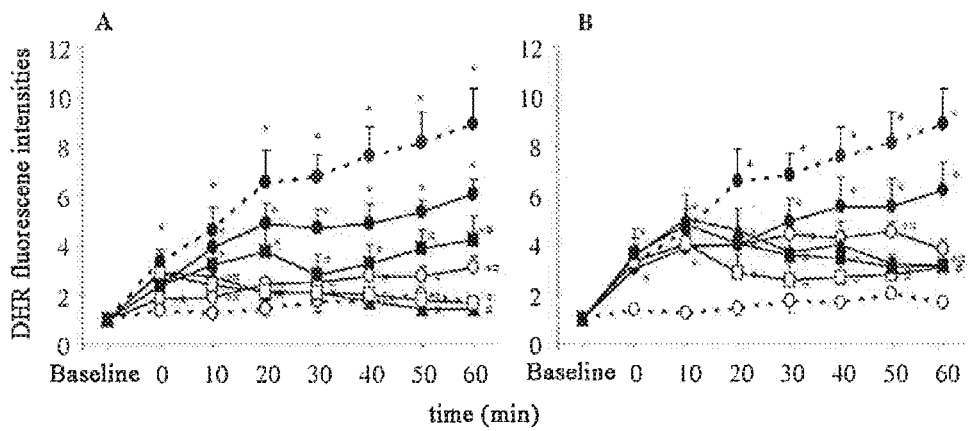
In FIG. 5, Sham indicates Sham operation group; I/R, I/R group; DLA+I/R. DLA pre-administration group; R1+I/R. R1 pre-administration group; DR(4:1)+I/R, the combination of DLA and R1 in a weight ratio of 4:1 pre-administration group; DR(1:1)+I/R, the combination of DLA and R1 in a weight ratio of 1:1 pre-administration group; DR(1:4)+I/R, the combination of DLA and R1 in a weight ratio of 1:4 pre-administration group; I/R+DLA, DLA post-administration group; I/R+R1. R1 post-administration group; I/R+DR (4:1), the combination of DLA and R1 in a weight ratio of 4:1 post-administration group; I/R+DR (1:1), the combination of DLA and R1 in a weight ratio of 1:1 post-administration group; I/R+DR (1:4), the combination of DLA and R1 in a weight ratio of 1:4 post-administration group. The results are expressed as mean±SE. * represents P<0.05, compared to the Sham group; # represents P<0.05, compared to the I/R group.
Figure 6:
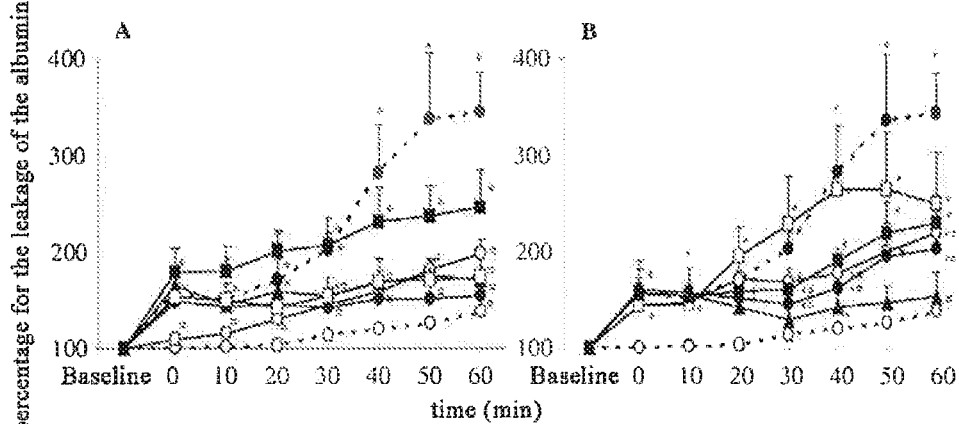
FIG. 6 illustrates the effects of DLA. R1 and their combinations on the plasma albumin leakage from the mesenteric venules of the rats after I/R. Only a small amount of plasma albumin was observed to be leakaged from the mesenteric venules of the rats in the Sham group at the end of a 60 min of the observation. Apparently, plasma albumin leakage from the mesenteric venules in the rats of I/R group were increased after the beginning of the reperfusion, which was further increased with the continuously ongoing reperfusion. A pre-administration of DLA:R1 (1:4) had no significant inhibitory effects on the plasma albumin leakage from the venules. But a pre-administration of DLA, R1, DR (4:1) or DR (1:1) had significant inhibitory effects on the plasma albumin leakage from the venules. A post-administration with DR (1:1) or DR (1:4) had no significant inhibitory effects on the plasma albumin leakage from the venules after reperfusion, whereas a post-administration with DLA. R1 or DR (4:1) had significant inhibitory effects on the plasma albumin leakage from the venules after reperfusion. A post-administration with DR (4:1) was confirmed to have the strongest inhibitory effect.
Figure 7:
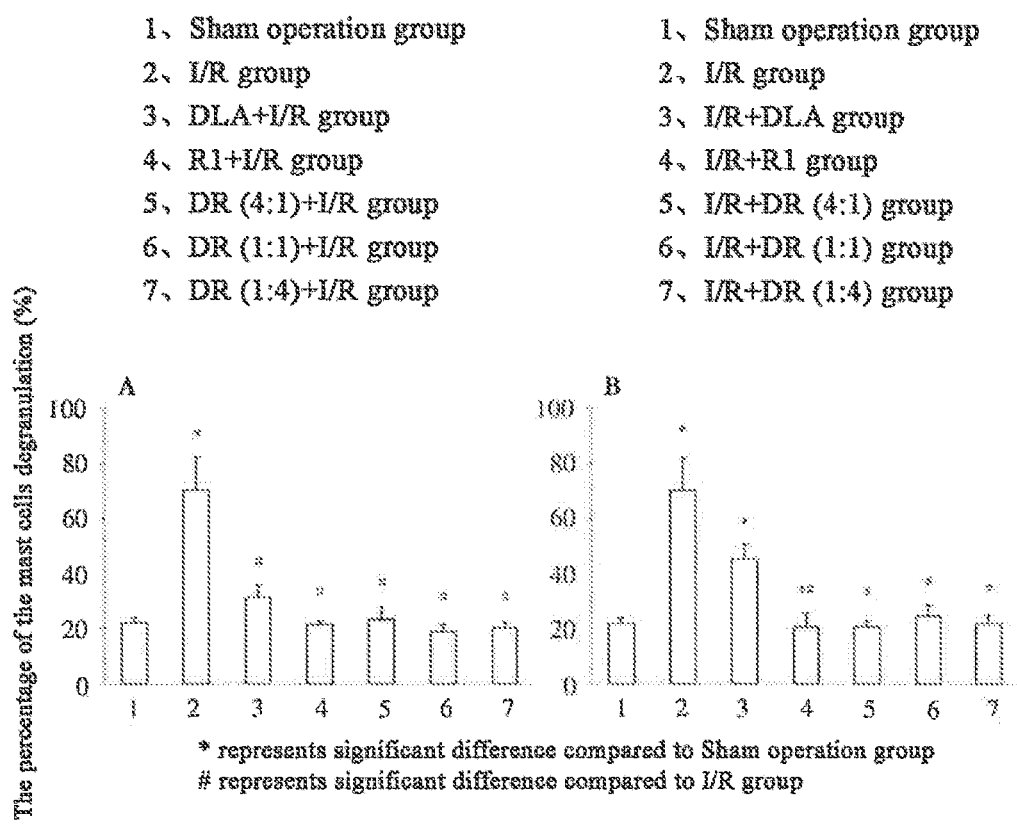
FIG. 7 illustrates the effects of DLA. R1 and their combinations on the mast cells degranulation in the mesenteric interstitial substance of the rats after I/R. Compared to the Sham group, there was a significant increase in the percentage of the mast cells degranulation in I/R group after 60 min of the reperfusion. A pre-administration with DLA. R1 or their combinations can significantly inhibit the increase in the percentage of the mast cells degranulation in the mesenteric interstitial substance of the rats caused by I/R. After reperfusion, a post-administration with DLA had no significant inhibitory effects on the percentage of the mast cells degranulation, whereas a post-administration with R1 or each combination of DR can significantly inhibit the increase in the percentage of the mast cells degranulation in the mesenteric interstitial substance of the rats caused by I/R.

1. After I/R, the diameters of the mesenteric venules of the rats have no obvious changes; the number of the leukocytes rolling along the venular walls increased; the number of the leukocytes adhered to the venules increased; the number of the leukocytes emigrated from the venules increased; DHR fluorescence intensities of the venular walls increased; the percentage of FITC-labeled plasma albumin leakage and the percentage of the mast cells degranulation increased significantly.

2. Pre-administration with DLA can inhibit the following symptoms caused by I/R: an increase in the number of leukocytes rolling along venular walls, an increase in the number of leukocytes adhered to inner walls of venules, an increase in the number of leukocytes emigrated from venules, a production of peroxides in venular wails, a leakage of plasma albumin from venules and an increase in a percentage of mast cells degranulation. A post-administration with DLA, however, has the same effects as those of the pre-administration, except without the significant inhibition on the rate of the mast cells degranulation.

3. Pre-administration and post-administration with R1 can inhibit the following symptoms caused by I/R: an increase in the number of leukocytes adhered to inner walls of venules, an increase in the number of leukocytes emigrated from venules, a leakage of plasma albumin from venules and an increase in a percentage of mast cells degranulation. Pre-administration or post-administration with R1 have no significant inhibitory effects on the diameters of the mesenteric venules and the leukocytes roiling along the mesenteric venules after I/R. R1 has no inhibitory effects on the increase of DHR fluorescence intensities of the mesenteric venular walls of the rats caused by I/R.

4. Post-administration with the combination of DLA and R1 in a weight ratio of 4:1 has the particularly significant effects on inhibiting the plasma albumin leakage from the venules caused by I/R.

5. Pre-administration with the combination of DLA and R1 in a weight ratio of 4:1 has the particularly significant effects on inhibiting the production of peroxides in the venular wall caused by I/R.

In summary, the present studies revealed that DLA. R1 or their combinations can treat and prevent a microcirculation disorder caused by I/R. Hence, they can be used for treating and/or preventing the diseases: caused by microcirculation disorder, e.g. allergic diseases (pollinosis, skin diseases, asthma and diarrhea), hyperlipidemia, hypertension, infection, mental stimulation, traumatic injury, microcirculation disorder caused by operation and interventional therapy etc.

EXAMPLES

The following examples are given only for purpose of illustration and do not intend to limit the scope of the invention in any way.

Example 1

Tablets

Formula:
DLA:R1=1:1 (by weight), a total amount of DLA and R1 is 105 g; microcrystalline cellulose 55 g; aerosil 3 g; magnesium stearate 1.5 g Process:
All of the raw materials and vehicles were sifted with a 100 mesh sieve. The DLA and R1 (1:1 by weight) and the microcrystalline cellulose were well mixed and prepared with a 60% ethanol aqueous solution as a binding agent to give soft materials. The obtained soft materials were passed through a 20 mesh sieve to prepare granules, the granules were dried at 60° C. and taken out to select the granules by using a 30 mesh sieve. Then, the aerosil and the magnesium stearate were added, well mixed to press into 1000 tablets.

Example 2

Tablets

Formula:
DLA:R1=1:4 (by weight), a total amount of DLA and R1 is 85 g; calcium sulfate 118 g, microcrystalline cellulose 37 g; aerosil 2.4 g; magnesium stearate 1.2 g Process:
All of the raw materials and vehicles were sifted with a 100 mesh sieve. The DLA and R1 (1:4 by weight), the microcrystalline cellulose and the calcium sulfate were well mixed and prepared with a 60% ethanol aqueous solution as a binding agent to give soft materials. The obtained soft materials were passed through a 20 mesh sieve to prepare granules, the granules were dried at 60° C. and taken out to select the granules by using a 30 mesh sieve. Then, the aerosil and the magnesium stearate were added, well mixed to press into 1000 tablets.

Example 3

Tablets

Formula:
DLA:R1=4:1 (by weight), a total amount of DLA and R1 is 133 g; calcium sulfate 208 g, microcrystalline cellulose 68 g; aerosil 5 g; magnesium stearate 2.5 g Process:
All of the raw materials and vehicles were sifted with a 100 mesh sieve. The DLA and R1 (4:1 by weight), the microcrystalline cellulose and the calcium sulfate were well mixed and prepared with a 60% ethanol aqueous solution as a binding agent to give soft materials. The obtained soft materials were passed through a 20 mesh sieve to prepare granules, the granules was dried at 60° C. and taken out to select the granules by using a 30 mesh sieve. Then, the aerosil and the magnesium stearate were added, well mixed to press into 1000 tablets.

Example 4

Capsules 60 g of DLA was weighted, into which adequate amounts of starch and magnesium stearate and the like were added, granulated and selected to load into #1 capsule to obtain the capsules.

Example 5

Oral Solutions 8 g of DLA was weighted, into which adequate amounts of sucrose and sorbic acid were added, water was added to a volume of 1000 ml and separately packaged into 10 ml/bottle, thereby oral solutions were obtained.

Example 6

Granules 80 g of R1 was weighted, into which adequate amounts of dextrin and stevioside were added, granulated by dry method, selected and separately packaged to obtain the granules.

Example 7

Injections 7 g of R1 was dissolved with water. Sodium chloride and ethyl paraben were dissolved with hot water. Both of the solutions were well mixed and the pH value was adjusted, diluted with water for injection to a volume of 1000 ml, filtered through hollow fiber membrane, filled, and sterilized to obtain the injections.

Example 8

Injections

DLA:R1=4:1 (by weight) with a total amount of 2 g was dissolved with water. Sodium chloride and ethyl paraben were dissolved with hot water. Both of the solutions were well mixed and the pH value was adjusted, diluted with water for injection to a volume of 1000 ml, filtered through hollow fiber membrane, filled, and sterilized to obtain the injections.

What is claimed is:

1. A method for treating at least one disease caused by a microcirculation disorder resulting from ischemia-reperfusion in a subject, the method comprising administering an effective amount of a first medicine prepared from a first combination of Danshensu and Notoginsenoside R1 to the subject, the Danshensu having a weight ratio relative to the Notoginsenoside R1 in a range of about 1:4 to about 4:1, wherein the at least one disease caused by the microcirculation disorder resulting from ischemia-reperfusion is selected from the group consisting of: pollinosis, asthma, diarrhea, hypertension, infection, and traumatic injury.

2. The method of claim 1, further comprising providing at least one of a pre-administration and a post-administration of a second medicine having a second combination of Danshensu and Notoginsenoside R1 to inhibit at least one symptom caused by ischemia-reperfusion, the at least one symptom selected from the group consisting of: an increase in the number of leukocytes adhered to inner walls of venules, an increase in the number of leukocytes emigrated from venules, a production of peroxides in venular walls, a leakage of plasma albumin from venules, and an increase in a percentage of mast cells degranulation.

3. The method of claim 1, wherein the first medicine comprises Danshensu having a weight ratio relative to the Notoginsenoside R1 in a range of about 1:2 to about 2:1.

4. The method of claim 2, wherein providing the post-administration with the second combination of Danshensu and Notoginsenoside R1 in a weight ratio of about 4:1 inhibits a leakage of the plasma albumin from venules caused by ischemia-reperfusion.

5. The method of claim 1, wherein the first medicine is a pharmaceutical composition prepared by using the first combination of Danshensu and Notoginsenoside R1 as an active component.

6. The method of claim 1, wherein each of the Danshensu and Notoginsenoside R1 in the first medicine has a purity of more than 50% by weight.

7. The method of claim 1, wherein each of the Danshensu and Notoginsenoside R1 in the first medicine has a purity of more than 90% by weight.

8. The method of claim 1, wherein each of the Danshensu and Notoginsenoside R1 in the first medicine has a purity of more than 98% by weight.

9. The method of claim 1, wherein the first medicine comprises Danshensu having a weight ratio relative to the Notoginsenoside R1 of about 1:1.

10. The method of claim 2, wherein the second medicine comprises Danshensu having a weight ratio relative to the Notoginsenoside R1 in a range of about 1:4 to about 4:1.

11. The method of claim 2, wherein the second medicine comprises Danshensu having a weight ratio relative to the Notoginsenoside R1 in a range of about 1:2 to about 2:1.

12. The method of claim 2, wherein the second medicine comprises Danshensu having a weight ratio relative to the Notoginsenoside R1 of about 1:1.

13. The method of claim 2, wherein providing the pre-administration with the second combination of Danshensu and Notoginsenoside R1 in a weight ratio of about 4:1 inhibits a production of peroxides in venular walls caused by ischemia-reperfusion.

\* \* \* \* \*